United States Patent
Engwall et al.

(10) Patent No.: US 11,446,517 B2
(45) Date of Patent: Sep. 20, 2022

(54) ASSIGNING RIPPLE FILTER SETTINGS TO A PLURALITY OF SUB-BEAMS

(71) Applicant: RaySearch Laboratories AB, Stockholm (SE)

(72) Inventors: Erik Engwall, Hägersten (SE); Martin Janson, Enskededalen (SE); Lars Glimelius, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 0 days.

(21) Appl. No.: 16/625,988

(22) PCT Filed: Jun. 28, 2018

(86) PCT No.: PCT/EP2018/067412
§ 371 (c)(1),
(2) Date: Dec. 23, 2019

(87) PCT Pub. No.: WO2019/002463
PCT Pub. Date: Jan. 3, 2019

(65) Prior Publication Data
US 2021/0154492 A1    May 27, 2021

(30) Foreign Application Priority Data
Jun. 30, 2017 (EP) ..................... 17178929

(51) Int. Cl.
*A61N 5/10* (2006.01)
(52) U.S. Cl.
CPC ........... *A61N 5/103* (2013.01); *A61N 5/1031* (2013.01); *A61N 2005/1087* (2013.01); *A61N 2005/1095* (2013.01)
(58) Field of Classification Search
CPC ........ A61N 5/10; A61N 5/103; A61N 5/1031; A61N 2005/1087; A61N 2005/1095
(Continued)

(56) References Cited

U.S. PATENT DOCUMENTS 6,639,234 B1 * 10/2003 Badura ................ A61N 5/1043
250/492.1
6,670,618 B1 * 12/2003 Hartmann ............ A61N 5/1043
250/491.1
(Continued)

FOREIGN PATENT DOCUMENTS

CN    102695964 A    9/2012
DE    102012210241 A1    12/2013
(Continued)

OTHER PUBLICATIONS

Yousuke Hara et al., Improvement of spread-out Bragg peak flatness for a carbon-ion beam by the use of a ridge filter with a ripple filter, Phys. Med. Biol. 57 1717 (2012). (Year: 2012).*
(Continued)

*Primary Examiner* — Allen C. Ho
(74) *Attorney, Agent, or Firm* — Faegre Drinker Biddle & Reath LLP (57) ABSTRACT

It is provided a method for determining ripple filter settings for an ion therapy beam being capable of providing ions of different energy levels to a target volume. The method is performed in a treatment planning system and comprises the steps of: determining at least one beam direction to use to cover a target volume; and assigning a ripple filter setting to each one of a plurality of sub-beams of each one of the at least one beam direction such that each sub-beam is assigned a different ripple filter setting, wherein each ripple filter setting results in a different effect on a Bragg-peak width in a direction along the ion therapy beam, and each energy level is assigned to one of the plurality of sub-beams. The step of assigning a ripple filter setting comprises optimising based on different filter settings for different sub-beams for each beam direction.

13 Claims, 5 Drawing Sheets

(58) Field of Classification Search
USPC .......................................................... 378/65
See application file for complete search history.

(56) References Cited

U.S. PATENT DOCUMENTS

| | | | | |
|---|---|---|---|---|
| 6,736,831 B1* | 5/2004 | Hartmann | ............ | A61N 5/1043 607/1 |
| 6,799,068 B1* | 9/2004 | Hartmann | ............ | A61N 5/1071 607/2 |
| 6,891,177 B1* | 5/2005 | Kraft | ..................... | A61N 5/1042 250/492.1 |
| 7,579,610 B2* | 8/2009 | Grözinger | ................. | A61N 5/10 250/492.3 |
| 8,039,822 B2* | 10/2011 | Rietzel | ................. | A61N 5/1043 250/492.3 |
| 8,299,448 B2* | 10/2012 | Bert | ..................... | A61N 5/1043 250/492.3 |
| 8,598,546 B2* | 12/2013 | Bert | ..................... | A61N 5/1043 250/492.3 |
| 8,987,690 B2* | 3/2015 | Kabasawa | ........... | H01J 37/3007 250/492.23 |
| 9,604,075 B2* | 3/2017 | Scholz | ................. | A61N 5/1031 |
| 9,878,181 B2* | 1/2018 | Russo | ................. | A61N 5/1031 |
| 10,912,953 B2* | 2/2021 | Wulff | ................... | A61N 5/1043 |
| 2009/0230327 A1 | 9/2009 | Rietzel | | |

FOREIGN PATENT DOCUMENTS

| | | |
|---|---|---|
| EP | 2510978 A1 | 10/2012 |
| TW | I589328 B | 7/2017 |

OTHER PUBLICATIONS

Yoshihisa Takada et al., A miniature ripple filter for filtering a ripple found in the distal part of a proton SOBP, Nuclear Instruments and Methods in Physics Research Section A 524 366 (2004). (Year: 2004).*

Uli Weber and Gerhard Kraft, Design and construction of a ripple filter for a smoothed depth dose distribution in conformal particle therapy, Phys. Med. Biol. 44 2765 (1999). (Year: 1999).*

First Examination Report issued Feb. 23, 2022 in Indian Patent Application No. 201917039253.

* cited by examiner

ASSIGNING RIPPLE FILTER SETTINGS TO A PLURALITY OF SUB-BEAMS

CROSS-REFERENCE TO RELATED APPLICATIONS

This application is a national stage application under 35 U.S.C. § 371 of International Application No. PCT/EP2018/067412, filed on Jun. 28, 2018, and claims benefit of European Patent Application No. 17178929.0, filed on Jun. 30, 2017, both of which are incorporated herein by reference in their entirety.

TECHNICAL FIELD

The invention relates to a method, a treatment planning system, a computer program and a computer program product for determining and assigning ripple filter settings for an ion therapy beam being capable of providing ions of different energy levels to a target volume.

BACKGROUND

In ion beam therapy, a beam of ions (e.g. protons or heavier ions, such as carbon ions) is directed towards a target volume. The target volume can e.g. represent a cancer tumour. The ions penetrate the tissue and deliver a dose of energy to destroy cancer cells. An advantage of ion beam therapy is that there is a significant peak in the dose distribution, known as the Bragg peak. The Bragg peak is a peak of dose delivery occurring at a certain depth, after which the dose delivery falls of quickly. This can be compared with electron beam therapy or X-ray therapy where the peak occurs very close to entering the tissue and dose fall off cannot be controlled with the same sharp fall off as for ion therapy.

The depth of the Bragg peak in the patient can be controlled by adjusting an energy amount of the ions. Lateral position can be controlled using electromagnets to deflect the beam. A spot in ion beam therapy refers to a collection of ions of a specific energy level at a specific lateral location. The number of particles delivered to a spot is commonly referred to as the spot weight. By providing doses in spots in many different locations in a three dimensional space, the target volume can be covered with a desired dose distribution. This procedure is called active scanning ion beam therapy, also known as pencil beam scanning.

The planning of how the spots should be delivered is performed in a treatment planning system. The treatment planning system determines a set of energy layers, each containing a distribution of spots. The energy layers are then communicated to the ion beam system, which delivers the ion beam. The treatment planning system and the ion beam system are connected in a way that is known in the art per se.

To ensure a smooth dose distribution in the depth direction, the distance between consecutive energy layers must be small enough relative the width of the Bragg peak. If the Bragg peaks are narrow, many energy layers are needed, which means that the treatment time is prolonged. To overcome this problem a device that broadens the Bragg peak, referred to as ripple filter, is often used in such situations. For most ion delivery systems, a substantial part of the delivery time is spent in switching energy, and therefore the reduction of the number of energy layers will have a major impact on the total delivery time.

SUMMARY

It is an object to determine an efficient combination of ripple filter settings for an ion therapy beam.

According to a first aspect, it is provided a method for determining ripple filter settings for an ion therapy beam being capable of providing ions of different energy levels to a target volume. The method is performed in a treatment planning system and comprises the steps of: determining at least one beam direction to use to cover a target volume; and assigning a ripple filter setting to each one of a plurality of sub-beams of each one of the at least one beam direction such that each sub-beam is assigned a different ripple filter setting, wherein each ripple filter setting results in a different effect on a Bragg peak width in a direction along the beam, and each energy level is assigned to one of the plurality of sub-beams. The step of assigning a ripple filter setting comprises the sub-steps of: determining a number of different ripple filter settings; generating, for each beam direction, one sub-beam for each ripple filter setting, resulting in one sub-beam for each ripple filter setting and beam direction, and populating each sub-beam with energy layers each comprising a plurality of spots, wherein each spot represents a collection of ions of a specific energy level at a specific lateral location; and optimising spots of all energy levels of all copies of all beam directions, by repeatedly varying a weight of at least a subset of the spots and calculating an effect on a performance measurement, until variations of the weights fail to improve the performance measurement more than a threshold amount, wherein the performance measurement is calculated by combining a plurality of evaluation criteria, wherein the plurality of evaluation criteria comprises a first criterion that improves the performance measurement when a total treatment time is reduced and a second criterion that improves the performance measurement when a desired dose distribution in the treatment volume is achieved.

Each sub-beam, when containing more than one energy level, may contain adjacent energy levels.

The step of assigning a ripple filter setting may comprise assigning, for the sub-beam with most distal Bragg peak, a ripple filter setting implying refraining from the use of a ripple filter.

The step of assigning a ripple filter setting may be performed based on a minimum Bragg peak width.

The step of assigning a ripple filter setting may be performed based on a maximum Bragg peak width.

The step of assigning a ripple filter setting may be performed based on geometries defined in a user configuration.

The geometries may be defined by target margins from a distal edge of a target volume.

The method may further comprise the step, after the step of optimising spots, of: finding, for each beam direction, any multi ripple filter region that is covered by energy layers with different ripple filter settings and with spots with weights above a threshold value; determining, in each multi ripple filter region, which single ripple filter setting to keep and removing the energy layers with other ripple filter settings in the multi ripple filter region; and returning to the step of optimising spots.

The step of determining which ripple filter setting to keep may comprise determining to keep a ripple filter setting according to a user parameter.

According to a second aspect, it is provided a treatment planning system for determining ripple filter settings for an ion therapy beam being capable of providing ions of different energy levels to a target volume. The treatment planning system comprises: a processor; and a memory storing instructions that, when executed by the processor, cause the treatment planning system to: determine at least one beam direction to use to cover a target volume; and assign a ripple filter setting to each one of a plurality of sub-beams of each one of the at least one beam direction such that each sub-beam is assigned a different ripple filter setting, wherein each ripple filter setting results in a different effect on a Bragg peak width in a direction along the beam, and each energy level is assigned to one of the plurality of sub-beams. The instructions to assign a ripple filter setting comprise instructions that, when executed by the processor, cause the treatment planning system to: determine a number of different ripple filter settings; generate, for each beam direction, one sub-beam for each ripple filter setting, resulting in one sub-beam for each ripple filter setting and beam direction, and populating each sub-beam with energy layers each comprising a plurality of spots, wherein each spot represents a collection of ions of a specific energy level at a specific lateral location; and optimise spots of all energy levels of all copies of all beam directions, by repeatedly varying a weight of at least a subset of the spots and calculating an effect on a performance measurement, until variations of the weights fail to improve the performance measurement more than a threshold amount, wherein the performance measurement is calculated by combining a plurality of evaluation criteria, wherein the plurality of evaluation criteria comprises a first criterion that improves the performance measurement when a total treatment time is reduced and a second criterion that improves the performance measurement when a desired dose distribution in the treatment volume is achieved.

Each sub-beam, when containing more than one energy level, may contain adjacent energy levels.

According to a third aspect, it is provided a treatment planning system for determining ripple filter settings for an ion therapy beam being capable of providing ions of different energy levels to a target volume. The treatment planning system comprises: means for determining at least one beam direction to use to cover a target volume; and means for assigning a ripple filter setting to each one of a plurality of sub-beams of each one of the at least one beam direction such that each sub-beam is assigned a different ripple filter setting, wherein each ripple filter setting results in a different effect on a Bragg peak width in a direction along the beam, and each energy level is assigned to one of the plurality of sub-beams. The means for assigning a ripple filter comprises: means for determining a number of different ripple filter settings; means for generating, for each beam direction, one sub-beam for each ripple filter setting, resulting in one sub-beam for each ripple filter setting and beam direction, and populating each sub-beam with energy layers each comprising a plurality of spots, wherein each spot represents a collection of ions of a specific energy level at a specific lateral location; and means for optimising spots of all energy levels of all copies of all beam directions, by repeatedly varying a weight of at least a subset of the spots and calculating an effect on a performance measurement, until variations of the weights fail to improve the performance measurement more than a threshold amount, wherein the performance measurement is calculated by combining a plurality of evaluation criteria, wherein the plurality of evaluation criteria comprises a first criterion that improves the performance measurement when a total treatment time is reduced and a second criterion that improves the performance measurement when a desired dose distribution in the treatment volume is achieved.

According to a fourth aspect, it is provided a computer program for determining ripple filter settings for an ion therapy beam being capable of providing ions of different energy levels to a target volume. The computer program comprises computer program code which, when run on a treatment planning system causes the treatment planning system to: determine at least one beam directions to use to cover a target volume; and assign a ripple filter setting to each one of a plurality of sub-beams of each one of the at least one beam direction such that each sub-beam is assigned a different ripple filter setting, wherein each ripple filter setting results in a different effect on a Bragg peak width in a direction along the beam, and each energy level is assigned to one of the plurality of sub-beams. The computer program code to assign a ripple filter setting comprises computer program code which causes the treatment planning system to: determine a number of different ripple filter settings; generate, for each beam direction, one sub-beam for each ripple filter setting, resulting in one sub-beam for each ripple filter setting and beam direction, and populating each sub-beam with energy layers each comprising a plurality of spots, wherein each spot represents a collection of ions of a specific energy level at a specific lateral location; and optimise spots of all energy levels of all copies of all beam directions, by repeatedly varying a weight of at least a subset of the spots and calculating an effect on a performance measurement, until variations of the weights fail to improve the performance measurement more than a threshold amount, wherein the performance measurement is calculated by combining a plurality of evaluation criteria, wherein the plurality of evaluation criteria comprises a first criterion that improves the performance measurement when a total treatment time is reduced and a second criterion that improves the performance measurement when a desired dose distribution in the treatment volume is achieved.

According to a fifth aspect, it is provided a computer program product comprising a computer program according to the fourth aspect and a computer readable means on which the computer program is stored.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

The invention is now described, by way of example, with reference to the accompanying drawings, in which.

DETAILED DESCRIPTION

The invention will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout the description.

According to embodiments presented herein, different ripple filter settings are applied for different sub-beams, where each sub-beam comprises one or more energy layers. In this way, the beneficial effects of the use of ripple filters can be exploited for proximal energy layers while a sharp distal fall-off is still achieved. The ripple filter settings are assigned based on different filter settings for different sub-beams for each beam direction.

Figure 1:
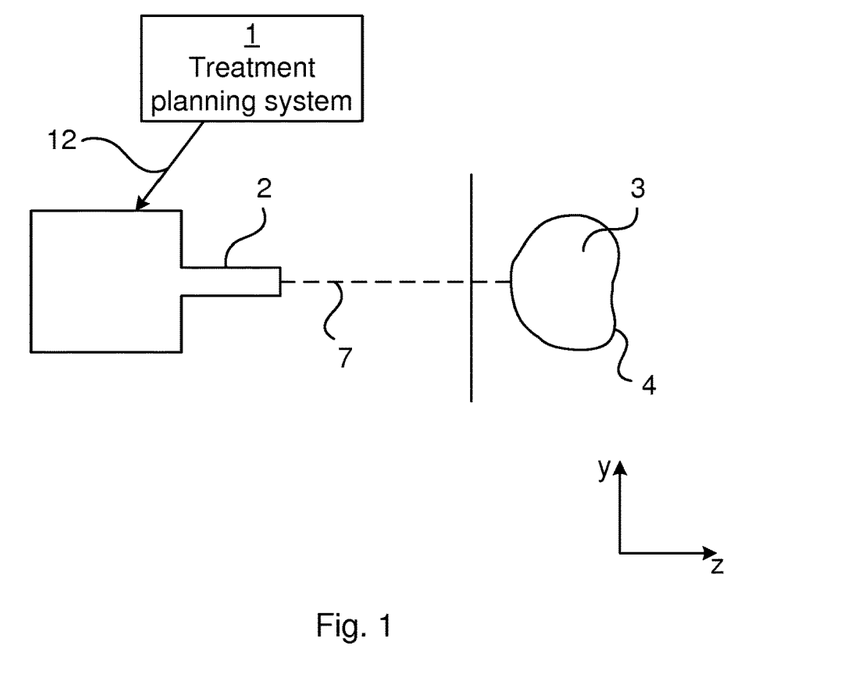
FIG. 1 is a schematic drawing illustrating an environment in which embodiments presented herein can be applied.

FIG. 1 is a schematic drawing illustrating an environment in which embodiments presented herein can be applied. A treatment planning system 1 determines a set of energy layers, each containing a distribution of spots for ion beam therapy. This is communicated as a treatment plan 12 to an ion beam system 2. Based on the treatment plan 12, the ion beam system 2 generates an ion beam 7 for providing spots to a target volume 3 of a patient. The target volume 3 is delimited by an edge 4.

In a coordinate system, the depth is represented along a z-axis and the y-axis is upwards in FIG. 1. The view in FIG. 1 can thus be considered to be a side view. The location of the dose maximum (Bragg peak) of the spot depth-wise, i.e. along the z-axis, is controlled by the kinetic energy of the ions; higher energy results in a deeper location of the dose maximum. Moreover, the lateral position, along the y-axis and x-axis (not shown in FIG. 1), is controlled using electromagnets to deflect the ion beam 7. In this way, spots can be provided to achieve a dose distribution covering the target volume 3 in three dimensions.

Figure 2:
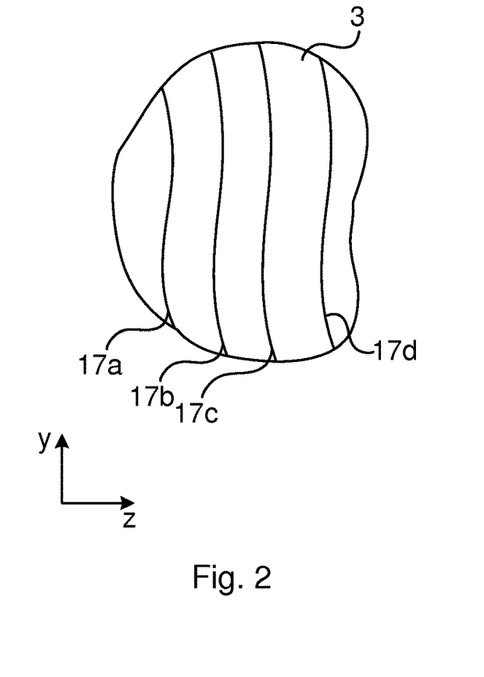
FIG. 2 is a schematic drawing illustrating the position of the Bragg peak for the different energy layers of the target volume of FIG. 1.

FIG. 2 is a schematic drawing illustrating the Bragg peak positions of the energy layers of the target volume 3 of FIG. 1. FIG. 2 is a side view, from the same perspective as the view of FIG. 1. As explained above, the depth (z-direction) of the Bragg peak depends on energy level. Here, the Bragg peak depths of four energy levels are shown 17a-d in the target volume 3. A first energy level 17a is illustrated by a line where the Bragg peaks occur for that energy level when the ion beam 7 of a first amount of energy, but with different lateral deflection are supplied using the ion beam therapy in the system of FIG. 1. A second energy level 17b is illustrated by a line where the Bragg peaks occur when ions of a second amount of energy are supplied, etc. It is to be noted that the density of tissue that the ion beam 7 passes through affects the depth. For instance, if the ion beam 7 passes through bone this results in a different depth of the Bragg peak than if the ion beam 7 passes through muscle tissue. Consequently, the Bragg peak depth of each energy level 17a-d does not need to be a straight line of a certain depth.

The separation between consecutive energy layers could be based on a user supplied water-equivalent distance, or automatically based on the Bragg peak width (in water) for those energy layers. The automatic selection of energy layers ensures a smooth dose distribution depth-wise, since the energy layers are placed close enough to each other relative the Bragg peak width. Another consequence is that more energy layers are needed where the Bragg peak is narrower, i.e. at shallow depths and when no ripple filter is used.

Figure 3:
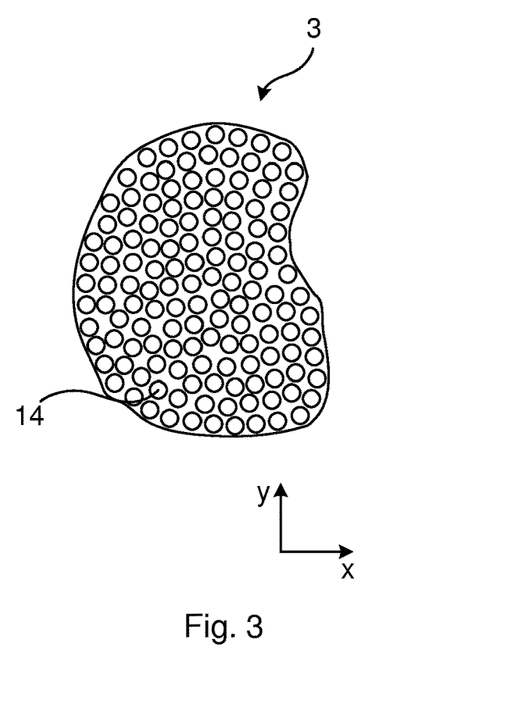
FIG. 3 is a schematic drawing illustrating the lateral distribution of spots in one of the energy layers of FIG. 2 according to one embodiment.

FIG. 3 is a schematic drawing illustrating the lateral distribution of spots in one of the energy layers (see 17a-d) of FIG. 2 according to one embodiment. The energy layer is shown along an x-y plane. While the energy layer does not need to be completely flat in the target volume 3 of the patient, the energy layer is here depicted as a flattened layer, as it would look if the patient were not present. The treatment planning system 1 can calculate the z position of the Bragg peak of any spot of each energy layer, and can thus transform any spot between a location on the energy layer, in a flattened two dimensional space, and a location of the Bragg peak in a three dimensional space, taking the tissue in the patient into account.

Spots 14 are provided throughout the energy layer to cover the target volume 3 at that energy layer. Even though not shown in FIG. 3, the size of the spots 14 can be different, and spots of different sizes can be provided in the same energy layer.

While FIG. 3 only discloses the spot distribution of one energy layer, there are corresponding spot distributions for each energy layer to be used for a target volume 3.

Figure 4:
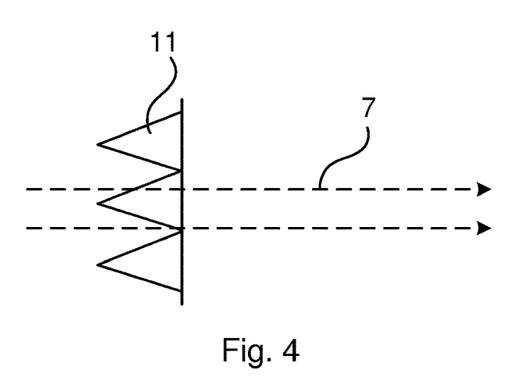
FIG. 4 is a schematic drawing illustrating the use of a ripple filter for the ion beam system of FIG. 1.

FIG. 4 is a schematic drawing illustrating the use of a ripple filter 11 for the ion beam system 2 of FIG. 1 according to one embodiment. The ripple filter 11 has in this example a triangular shaped cross section and forms part of the ion beam system (see 2 of FIG. 1).

Figure 5:
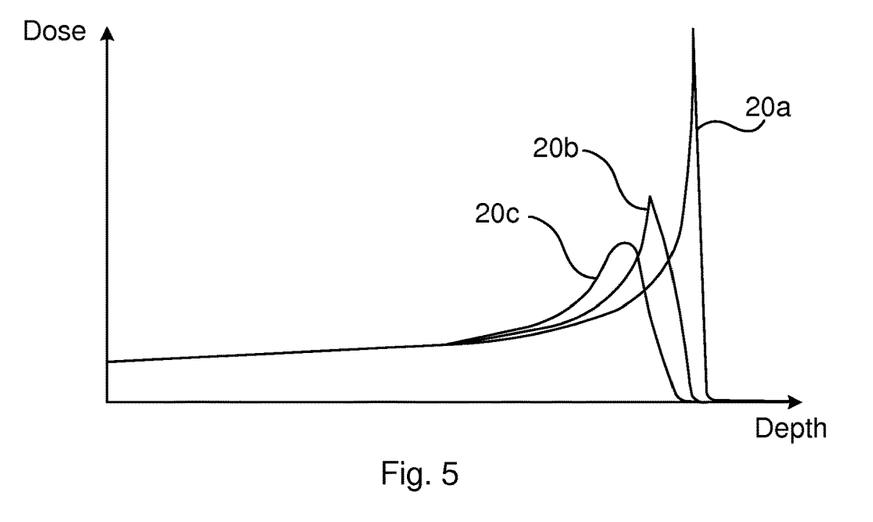
FIG. 5 is a schematic graph illustrating the effect different ripple filter settings have on a Bragg peak.

Ions of the ion beam 7 that pass through the peak of the triangle will traverse more material and lose more energy. Therefore, their range will be shorter than the ions of the ion beam 7 that pass through the outer parts of the triangles. The effect, when a large number of ions pass this type of repeated structure, will be a widening of the Bragg peak, as well as a reduced mean range of the protons, as shown in FIG. 5, described below. Hence, the ion beam 7 passes through the ripple filter 11 and its energy is dispersed along the direction of the beam (z-direction).

It is to be noted that any other type of filter achieving the same effect of widening the Bragg peak can equally well be applied; the filter does not need to be implemented as shown in FIG. 4. Different ripple filter settings could also refer to the use of different combinations of ripple filters applied concurrently.

FIG. 5 is a schematic graph illustrating the effect different ripple filter settings have on a Bragg peak. The horizontal axis represents depth in water and the vertical axis represents dose.

A first curve 20a shows dose distribution when no ripple filter is applied, also known as a pristine curve. A second curve 20b shows dose distribution when a first ripple filter is applied. A third curve 20c shows dose distribution when a second, thicker, ripple filters is applied.

The Bragg peak is the peak of each curve, which appears just prior to the dose dropping off. It can be seen how the Bragg peak of the pristine curve 20a is higher and narrower than the other curves 20*b-c*. The Bragg peak of the second curve 20*b*, where the thinner ripple filter is applied, is of medium height and medium width. The Bragg peak of the third curve 20*c*, where a thicker ripple filter is applied, is the lowest and also the widest. Also, the depth of the Bragg peak is reduced with more ripple filter effect.

Hence, different ripple filter settings result in different effects on the Bragg peak width (in a direction along the beam). The Bragg peak width can be defined as the width of the Bragg peak at a certain percentage of the maximum dose, e.g. the difference in depths of the 80% proximal dose level and the 80% distal dose level.

Figure 6:
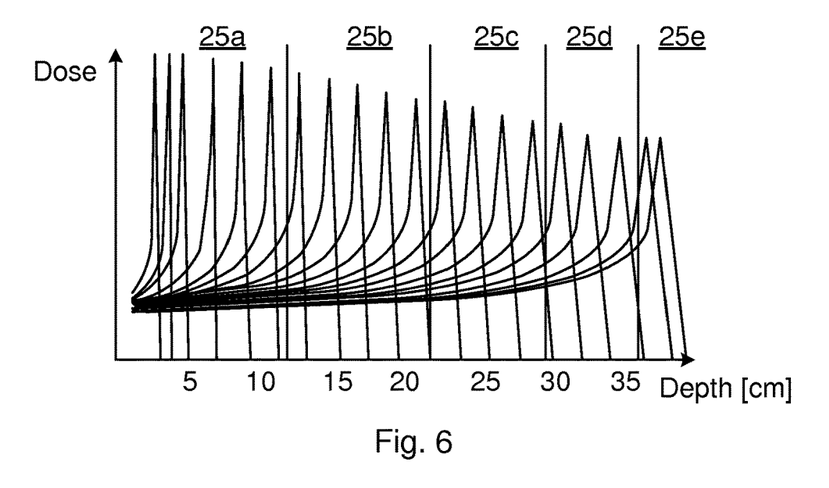
FIG. 6 is a schematic graph illustrating Bragg peaks of different energies and different sub-beams.

FIG. 6 is a schematic graph illustrating Bragg peaks of different energies. The curves, from left to right, represent gradually increased energy levels. This can be compared with FIG. 2, where the energy layers are shown, although for a smaller number of energy levels.

With increased energy, the Bragg peak goes deeper. This also means that more matter is traversed, with the consequence that the Bragg peak gets wider and lower.

According to embodiments herein, different ripple settings are assigned to different sub-beams 25*a-e*. Each sub-beam 25*a-e* contains one or more energy levels. In this example, the first six energy levels, in an increasing depth direction, are assigned to a first sub-beam 25*a*. The following five energy levels, in an increasing depth direction, are assigned to a second sub-beam 25*b*. The following four energy levels, in an increasing depth direction, are assigned to a third sub-beam 25*c*. The following three energy levels, in an increasing depth direction, are assigned to a fourth sub-beam 25*d*. The final two energy levels, in an increasing depth direction, are assigned to a fifth sub-beam 25*e*.

Each sub-beam 25*a-e* is then assigned a different ripple filter setting.

Looking for example at the first sub-beam 25*a*, the Bragg peaks are very narrow, which means that more layers might need to be added to avoid deep dose valleys between the Bragg peaks. However, increasing the number of energy layers will lead to a prolonged treatment time. In comparison, the Bragg peaks of the fifth sub-beam 25*e* are much wider and no additional energy layers nor use of ripple filters will be needed.

It is beneficial to increase the width of the more narrow Bragg peaks to reduce treatment time, while at the same time not using the same ripple filter setting for the fifth sub-beam 25*e* to avoid the broadening of the most distal Bragg peaks. It is beneficial to have a narrower Bragg peak at the greatest depth (the fifth sub-beam 25*e*) in order to keep the distal fall-off sharp, to thereby reduce any unwanted dose beyond the edge of the target volume. Hence, the first sub-beam 25*a* can be assigned a ripple filter setting with the greatest ripple filter effect, while the fifth sub-beam can be assigned a ripple filter setting with the least ripple filter effect (e.g. no ripple filter at all). The sub-beams 25*b-d* in between can be assigned ripple filter settings with gradually decreased ripple filter effect, in an increasing depth direction.

Figure 7:
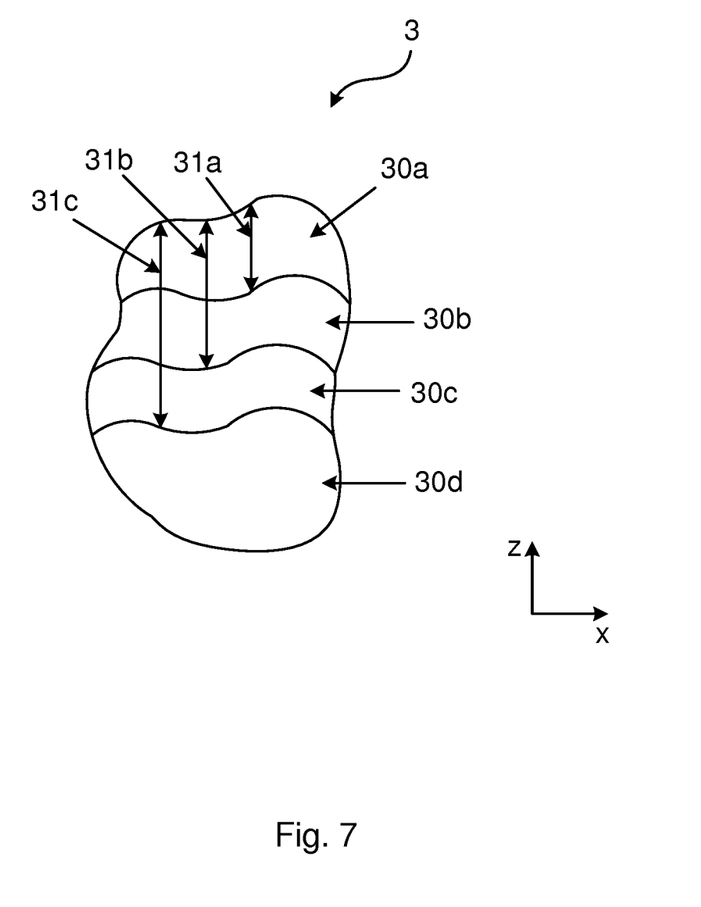
FIG. 7 is a schematic graph illustrating target sections defined by margins from a distal edge of a target volume.

FIG. 7 is a schematic graph illustrating target sections defined by margins from a distal edge of a target volume. There are here four different target sections 30*a-d*. A first target margin 31*a* is defined as the distance between the distal border of the second target section 30*b* and the distal edge of the target volume 3. A second target margin 31*b* is defined as the distance between the distal border of the third target section 30*c* and the distal edge of the target volume 3. A third target margin 31*c* is defined as the distance between the distal border of the fourth target section 30*d* and the distal edge of the target volume 3.

Figure 8A:
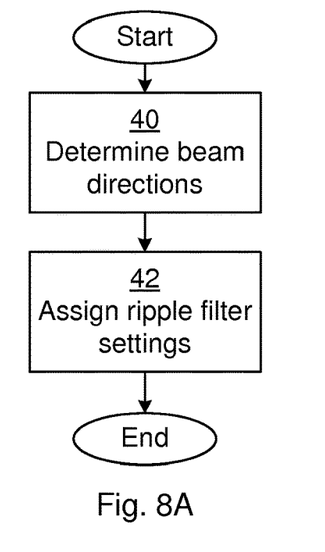
FIGS. 8A-B are flow charts illustrating embodiments of methods for determining ripple filter settings, the method being performed in the treatment planning system of FIG. 1.
Figure 8B:
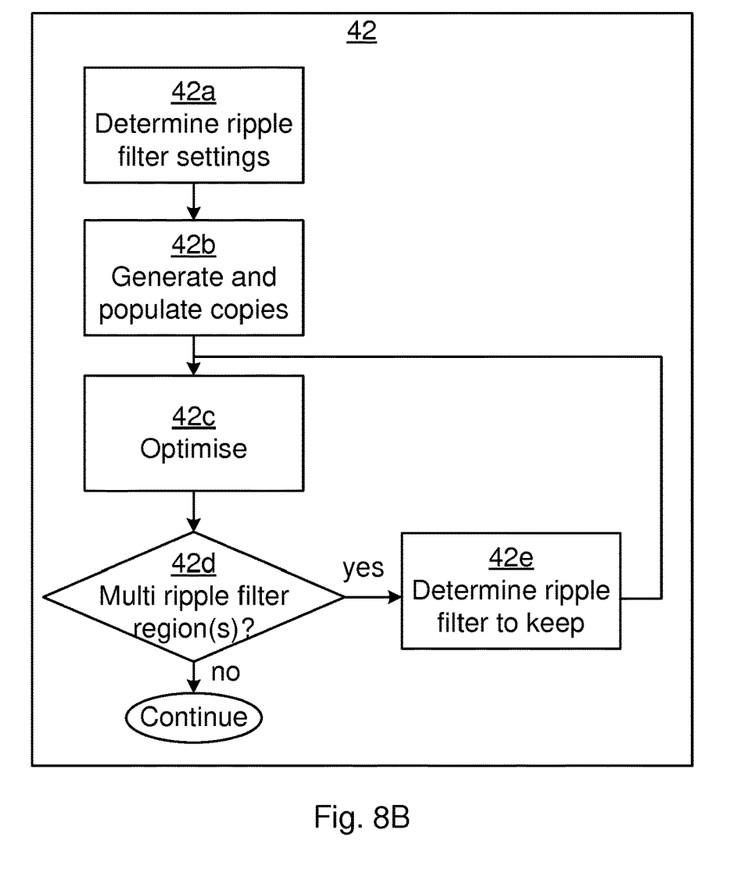

FIGS. 8A-B are flow charts illustrating embodiments of methods for determining ripple filter settings. The method is performed in the treatment planning system (see 1 of FIG. 1). In the following, a conditional step is a step where the method forks in two different possible paths. An optional step is a step that does not need to be performed. First, the method of FIG. 8A will be described.

In a determine beam directions step 40, at least one beam directions to use to cover a target volume is determined.

In an assign ripple filter settings step 42, the treatment planning system assigns a ripple filter setting to each one of a plurality of sub-beams of each one of the at least one beam direction. This is performed such that each sub-beam is assigned a different ripple filter setting. Each ripple filter setting results in a different effect on a Bragg peak width, in a direction along the beam (i.e. the z-direction). Moreover, each energy level is assigned to one of the plurality of sub-beams.

In one embodiment, e.g. as illustrated in FIG. 6 and described above, each sub-beam, when containing more than one energy level, contains adjacent energy levels. In other words, in such a case, the sub-beams to not overlap in terms of energy levels.

Optionally, a ripple filter setting implying refraining from the use of a ripple filter is assigned for the sub-beam with most distal Bragg peak. As explained above, this provides the sharpest fall-off, which can be useful for the most distal Bragg peak. Distal is to be interpreted as further along the beam direction, i.e. the z-direction.

The assign ripple filter settings step 42 can be based on a user configured or determined minimum Bragg peak width and/or a maximum Bragg peak width. In the simplest form with only a minimum Bragg peak width defined, the result will be just one ripple filter setting. In a more complex situation, there could be a combination of a minimum and a maximum Bragg peak width defined. This will result in several sub-beams: starting to assign energy layers from the distal edge, the choice of ripple filter setting will be based on a setting resulting in a Bragg peak width that is smaller than, or equal to the defined maximum Bragg peak width, but larger than, or equal to the minimum Bragg peak width. When adding more energy layers with lower and lower energy, the Bragg peak width will decrease and eventually the minimum Bragg peak width will not be reached, and a new ripple filter setting needs to be chosen. Continuing this process all the way to the proximal edge, several sub-beams with different ripple filter settings are created.

If the minimum Bragg peak width cannot be reached even with the largest ripple filter setting, the largest ripple filter setting will still be chosen. Equivalently, if the maximum Bragg peak width is exceeded even with the smallest ripple filter setting, the smallest ripple filter setting will be chosen. It should be noted that refraining the use any ripple filters at all is also defined as a ripple filter setting.

Optionally, the ripple filter settings are based on geometries defined in a user configuration. For instance, the geometries can be defined by target margins from a distal edge of a target volume as shown in FIG. 7. The combination of distal target margins creates target sections 30*a-d*, where different ripple filter settings will be applied. As an alternative, the geometries can be defined using other tools in the treatment planning system for delineation of volumes.

The ripple filter settings in each geometry could be set directly by the user, or each geometry could have its own minimum or maximum Bragg peak width defined.

Looking now to FIG. 8B, embodiments of the assign ripple filter settings step 42 are described in some more detail. The embodiments shown here are based on using optimisation.

In a determine ripple filter settings step 42a, a number of (available) different ripple filter settings is determined. For instance, there may be five different ripple filter settings.

In a generate and populate copies step 42b, the treatment planning system generates, for each beam direction, one sub-beam for each ripple filter setting. This results in one sub-beam for each ripple filter setting and beam direction. Furthermore, the treatment planning system populates each sub-beam with energy layers each comprising a plurality of spots. As described above, each spot represents a collection of ions of a specific energy level at a specific lateral location.

In a optimise step 42c, the treatment planning system optimises spots of all energy levels of all copies of all beam directions, by repeatedly varying a weight of at least a subset of the spots and calculating an effect on a performance measurement. This continues until variations of the weights fail to improve the performance measurement more than a threshold amount. The performance measurement is calculated by combining a plurality of evaluation criteria. The plurality of evaluation criteria comprises a first criterion that improves the performance measurement when a total treatment time is reduced and a second criterion that improves the performance measurement when a desired dose distribution in the treatment volume is achieved.

The first criterion aims at reducing the treatment time. The largest gain in treatment time, when switching from one ripple filter setting, which results in narrow Bragg peaks, to another setting, which results in broader Bragg peaks, can be found in the reduction of the number of energy layers, and thus in the reduction of the accumulated energy switching time. The energy switching time is not related to the spot weight (and actual delivery) of a specific spot. In the context of optimisation with respect to variation of spot weights, the first criterion comprises a spot specific measure, which relates each spot to the energy switching time. Such a measure is ripple filter setting dependent and can be directly or indirectly related to the delivery time. It can be formulated in a number of different ways, and can for example be based on:
  a) ripple filter setting. A ripple filter setting resulting in broader Bragg peaks, as compared to a setting resulting in narrower Bragg peaks, reduces the treatment time. Each spot in a specific sub-beam is related to the ripple filter setting of that sub-beam.
  b) energy layer spacing. Larger as compared to smaller energy layer spacing will reduce the treatment time. Each spot in a specific layer of a specific sub-beam assigned a quantity related to the energy layer spacing. This quantity could for example be the shortest water-equivalent distance to any of the adjacent energy layers, and would then be the same for all spots in one energy layer.
  c) delivery time of a sub-beam. For this measure, the total delivery time for each sub-beam is estimated. Each spot in a specific sub-beam is assigned a quantity, which is directly proportional to the delivery time of that sub-beam. As an alternative, each spot in a sub-beam could be assigned a quantity directly proportional to the accumulated energy switching time. For both alternatives, the assigned quantity is identical for all spots in the same sub-beam.

Other measures that directly or indirectly reduces the treatment time or reduces the number of energy layers could also be used.

In the optimise step 42c, the weights of the spots are, as mentioned above, repeatedly varied to improve the performance measurement. The dose distribution is directly altered by changing the weight of the spots, and there is a direct relation between the spot weights and the effect on the performance measurement for the second criterion, relating to dose distribution. For the first criterion, relating to treatment time, there is no such direct relation. The treatment time measures described above are related to energy switching time between delivery of the individual spots and are therefore not explicitly dependent on the spot weights. However, since the optimisation is performed with respect to the spot weights, an artificial relation between the spot weights and treatment time measures is established, such that the performance measurement related to the first evaluation criterion is improved when the spot weight is increased for spots with a favourable measure (ripple filter setting resulting in wide Bragg peaks, large energy layer spacing, short delivery time). As an example, when basing the first criterion on the energy layer spacing, this could be achieved in the optimisation by penalizing high spot weights for spots with smaller assigned energy layer spacing, which in turn will favour higher spot weights for spots with larger assigned energy layer spacing.

In a final sub-step of the optimise step 42c, a spot filtering is performed. The spot filtering removes spots with weights below a certain threshold value, which can be set by the user or directly by the system based on the capabilities of the ion delivery system In an optional conditional multi ripple filter region(s) step 42d, the treatment planning system determines whether it can find, for each beam direction, any multi ripple filter region that is covered by energy layers with different ripple filter settings and with spots with weights above a threshold value. The multi ripple filter region extends in the depth direction and is delimited by an energy interval. If any multi ripple filter region is found, the method proceeds to an optional determine ripple filter to keep step 42e. Otherwise, the method continues.

In the optional determine ripple filter to keep step 42e, the treatment planning system determines, in each multi ripple filter region, which single ripple filter setting to keep. The energy layers with other ripple filter settings in the multi ripple filter region are removed. A way to determine which ripple filter setting to keep could for example be based on the ripple filter setting, or the accumulated spot weight in the energy interval, or a combination of these parameters. The ripple filter setting to keep could also be determined according to a user defined parameter. After this step, there are no energy intervals with overlapping ripple filter settings and the method returns to the optimise step 42c.

Figure 9:
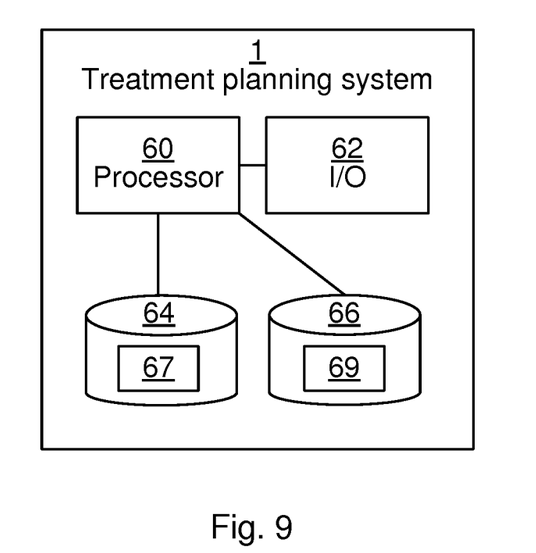
FIG. 9 is a schematic diagram illustrating components of the treatment planning system of FIG. 1 according to one embodiment.

FIG. 9 is a schematic diagram illustrating components of the treatment planning system 1 of FIG. 1 according to one embodiment. A processor 60 is provided using any combination of one or more of a suitable central processing unit (CPU), multiprocessor, microcontroller, digital signal processor (DSP), application specific integrated circuit etc., capable of executing software instructions 67 stored in a memory 64, which can thus be a computer program product. The processor 60 can be configured to execute the method described with reference to FIGS. 8A-B above.

The memory 64 can be any combination of random access memory (RAM) and read only memory (ROM). The memory 64 also comprises persistent storage, which, for example, can be any single one or combination of magnetic memory, optical memory, solid-state memory or even remotely mounted memory.

A data memory 66 is also provided for reading and/or storing data during execution of software instructions in the processor 60. The data memory 66 can be any combination of random access memory (RAM) and read only memory (ROM). The data memory 66 can e.g. contain a ripple filter settings 69.

The treatment planning system 1 further comprises an I/O interface 62 for communicating with other external entities. Optionally, the I/O interface 62 also includes a user interface.

Other components of the treatment planning system 1 are omitted in order not to obscure the concepts presented herein.

Figure 10:
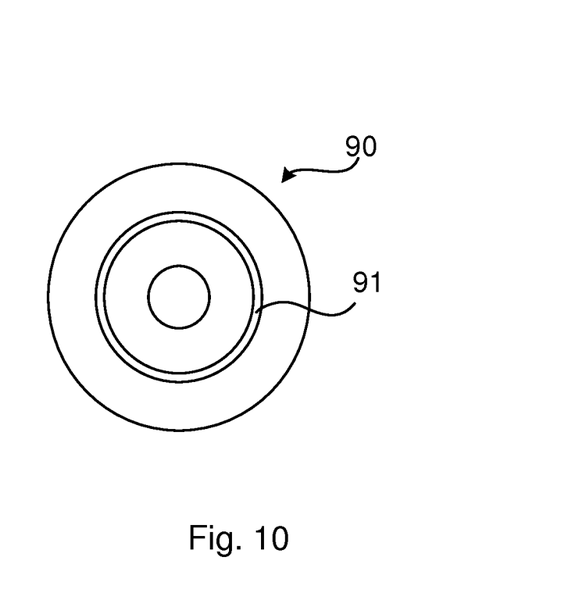
FIG. 10 shows one example of a computer program product comprising computer readable means.

FIG. 10 shows one example of a computer program product 90 comprising computer readable means. On this computer readable means, a computer program 91 can be stored, which computer program can cause a processor to execute a method according to embodiments described herein. In this example, the computer program product is an optical disc, such as a CD (compact disc) or a DVD (digital versatile disc) or a Blu-Ray disc. As explained above, the computer program product could also be embodied in a memory of a device, such as the computer program product 64 of FIG. 9. While the computer program 91 is here schematically shown as a track on the depicted optical disk, the computer program can be stored in any way which is suitable for the computer program product, such as a removable solid state memory, e.g. a Universal Serial Bus (USB) drive.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A method for determining ripple filter settings for an ion therapy beam being capable of providing ions of different energy levels to a target volume, the method being performed in a treatment planning system and comprising the steps of:
   determining at least one beam direction to use to cover a target volume; and
   assigning a ripple filter setting to each one of a plurality of sub-beams of each one of the at least one beam direction such that each sub-beam of the plurality of sub-beams is assigned a different ripple filter setting, wherein each ripple filter setting results in a different effect on a Bragg-peak width in a direction along the ion therapy beam, and each energy level is assigned to one of the plurality of sub-beams;
   wherein the step of assigning a ripple filter setting comprises the sub-steps of:
   determining a number of different ripple filter settings;
   generating, for each beam direction of the at least one beam direction, one sub-beam for each ripple filter setting, resulting in one sub-beam for each ripple filter setting and each beam direction, and populating each sub-beam with energy layers, each energy layer of the energy layers comprising a plurality of spots, wherein each spot of the plurality of spots represents a collection of ions of a specific energy level at a specific lateral location;
   optimizing spots of all energy levels of all copies of all beam directions by repeatedly varying a weight of at least a subset of the spots; and
   calculating an effect on a performance measurement until variations of the weight fail to improve the performance measurement by more than a threshold amount, wherein the performance measurement is calculated by combining a plurality of evaluation criteria, wherein the plurality of evaluation criteria comprises a first criterion that improves the performance measurement when a total treatment time is reduced and a second criterion that improves the performance measurement when a desired dose distribution in the target volume is achieved.

2. The method according to claim 1, wherein each sub-beam, when containing more than one energy level, contains adjacent energy levels.

3. The method according to claim 2, wherein the step of assigning a ripple filter setting further comprises:
   assigning, for a sub-beam of the plurality of sub-beams with a most distal Bragg peak, a ripple filter setting implying refraining from a use of a ripple filter.

4. The method according to claim 1, wherein the step of assigning a ripple filter setting further comprises:
   assigning the ripple filter setting based on a minimum Bragg-peak width.

5. The method according to claim 1, wherein the step of assigning a ripple filter setting further comprises:
   assigning the ripple filter setting based on a maximum Bragg-peak width.

6. The method according to claim 1, wherein the step of assigning a ripple filter setting further comprises:
   assigning the ripple filter setting based on geometries defined in a user configuration.

7. The method according to claim 6, wherein the geometries are defined by target margins from a distal edge of a target volume.

8. The method according to claim 1, wherein the step of optimizing spots further comprises:
   performing a spot filtering to remove spots with weights below a threshold value.

9. The method according to any one of the preceding claims, further comprising the step, after the step of optimizing spots, of:
   finding, for each beam direction of the at least one beam direction, any multi ripple filter region that is covered by energy layers with different ripple filter settings and with spots with weights above a threshold value;
   determining, in each multi ripple filter region, a single ripple filter setting to keep and removing energy layers with other ripple filter settings in the multi ripple filter region; and
   returning to the step of optimizing spots.

10. The method according to claim 9, wherein the step of determining, in each multi ripple filter region, a single ripple filter setting further comprises:
    determining the single ripple filter setting to keep according to a user parameter.

11. A treatment planning system for determining ripple filter settings for an ion therapy beam being capable of providing ions of different energy levels to a target volume, the treatment planning system comprising:
    a processor; and
    a memory storing instructions that, when executed by the processor, cause the processor to:
    determine at least one beam direction to use to cover a target volume; and assign a ripple filter setting to each one of a plurality of sub-beams of each one of the at least one beam direction such that each sub-beam of the plurality of sub-beams is assigned a different ripple filter setting, wherein each ripple filter setting results in a different effect on a Bragg-peak width in a direction along the ion therapy beam, and each energy level is assigned to one of the plurality of sub-beams;

wherein the instructions to assign a ripple filter setting comprise instructions that, when executed by the processor, cause the processor to:

determine a number of different ripple filter settings;

generate, for each beam direction of the at least one beam direction, one sub-beam for each ripple filter setting, resulting in one sub-beam for each ripple filter setting and each beam direction, and populating each sub-beam with energy layers, each energy layer of the energy layers comprising a plurality of spots, wherein each spot of the plurality of spots represents a collection of ions of a specific energy level at a specific lateral location;

optimize spots of all energy levels of all copies of all beam directions by repeatedly varying a weight of at least a subset of the spots; and calculating an effect on a performance measurement until variations of the weight fail to improve the performance measurement by more than a threshold amount, wherein the performance measurement is calculated by combining a plurality of evaluation criteria, wherein the plurality of evaluation criteria comprises a first criterion that improves the performance measurement when a total treatment time is reduced and a second criterion that improves the performance measurement when a desired dose distribution in the target volume is achieved.

12. A treatment planning system for determining ripple filter settings for an ion therapy beam being capable of providing ions of different energy levels to a target volume, the treatment planning system comprising one or more processors and a non-transitory computer-readable medium including one or more sequences of instructions that, when executed by the one or more processors, cause the one or more processors to:

determine at least one beam direction to use to cover a target volume; and assign a ripple filter setting to each one of a plurality of sub-beams of each one of the at least one beam direction such that each sub-beam of the plurality of sub-beams is assigned a different ripple filter setting, wherein each ripple filter setting results in a different effect on a Bragg-peak width in a direction along the ion therapy beam, and each energy level is assigned to one of the plurality of sub-beams;

wherein the one or more sequences of instructions further cause the one or more processors to assign a ripple filter by:

determining a number of different ripple filter settings;

generating, for each beam direction of the at least one beam direction, one sub-beam for each ripple filter setting, resulting in one sub-beam for each ripple filter setting and each beam direction, and populating each sub-beam with energy layers, each energy layer of the energy layers comprising a plurality of spots, wherein each spot of the plurality of spots represents a collection of ions of a specific energy level at a specific lateral location;

optimizing spots of all energy levels of all copies of all beam directions by repeatedly varying a weight of at least a subset of the spots; and calculating an effect on a performance measurement until variations of the weight fail to improve the performance measurement by more than a threshold amount, wherein the performance measurement is calculated by combining a plurality of evaluation criteria, wherein the plurality of evaluation criteria comprises a first criterion that improves the performance measurement when a total treatment time is reduced and a second criterion that improves the performance measurement when a desired dose distribution in the target volume is achieved.

13. A non-transitory computer-readable medium having stored thereon a computer program for determining ripple filter settings for an ion therapy beam being capable of providing ions of different energy levels to a target volume, the computer program comprising computer program code which, when executed by one or more processors of a treatment planning system, causes the treatment planning system to:

determine at least one beam direction to use to cover a target volume; and assign a ripple filter setting to each one of a plurality of sub-beams of each one of the at least one beam direction such that each sub-beam of the plurality of sub-beams is assigned a different ripple filter setting, wherein each ripple filter setting results in a different effect on a Bragg-peak width in a direction along the ion therapy beam, and each energy level is assigned to one of the plurality of sub-beams;

wherein the computer program code to assign a ripple filter setting comprises computer program code which, when executed by the one or more processors of the treatment planning system, causes the treatment planning system to:

determine a number of different ripple filter settings;

generate, for each beam direction of the at least one beam direction, one sub-beam for each ripple filter setting, resulting in one sub-beam for each ripple filter setting and beam direction, and populating each sub-beam with energy layers, each energy layer of the energy layers comprising a plurality of spots, wherein each spot of the plurality of spots represents a collection of ions of a specific energy level at a specific lateral location;

optimize spots of all energy levels of all copies of all beam directions by repeatedly varying a weight of at least a subset of the spots; and calculate an effect on a performance measurement until variations of the weight fail to improve the performance measurement by more than a threshold amount, wherein the performance measurement is calculated by combining a plurality of evaluation criteria, wherein the plurality of evaluation criteria comprises a first criterion that improves the performance measurement when a total treatment time is reduced and a second criterion that improves the performance measurement when a desired dose distribution in the target volume is achieved.

* * * * *